United States Patent [19]
Miyamoto et al.

[11] Patent Number: 4,749,515
[45] Date of Patent: Jun. 7, 1988

[54] LIQUID DETERGENT COMPOSITION

[75] Inventors: Nobuo Miyamoto; Takashi Ikeuchi; Zentaro Shinjo, all of Tokyo, Japan

[73] Assignee: Lion Corporation, Tokyo, Japan

[21] Appl. No.: 927,454

[22] Filed: Nov. 6, 1986

[30] Foreign Application Priority Data

Nov. 6, 1985 [JP] Japan ................................. 60-249493

[51] Int. Cl.⁴ ........................ C11D 1/10; C11D 1/12; C11D 3/30; C11D 3/34
[52] U.S. Cl. .................... 252/545; 252/546; 252/557; 252/DIG. 5; 252/DIG. 13
[58] Field of Search ......... 252/545, 546, 557, DIG. 5, 252/DIG. 13

[56] References Cited

U.S. PATENT DOCUMENTS

| | | | |
|---|---|---|---|
| 3,663,459 | 5/1972 | Yoshida et al. | 252/546 |
| 4,076,800 | 2/1978 | Marsh et al. | 424/70 |
| 4,273,684 | 6/1981 | Nagashima et al. | 252/546 |
| 4,591,498 | 5/1986 | Kawase et al. | 252/546 |
| 4,620,976 | 11/1986 | Quack et al. | 252/545 |

FOREIGN PATENT DOCUMENTS

| | | | |
|---|---|---|---|
| 2709750 | 9/1978 | Fed. Rep. of Germany | 252/546 |
| 5819 | 2/1971 | Japan | 252/545 |
| 1077470 | 7/1967 | United Kingdom | 252/546 |

OTHER PUBLICATIONS

"Maypons for Cosmetics", Trade Literature from Maywood Chemical Works (Division, Stepan Chem. Co.), Maywood, NJ, 1955.

Zussman, et al., "Acylated Amino Acids in Shampoos", *Journal of the Society of Cosmetic Chemists*, vol. 6, No. 5, Dec. 1955.

*Primary Examiner*—Paul Lieberman
*Assistant Examiner*—Linda D. Skaling
*Attorney, Agent, or Firm*—Birch, Stewart, Kolasch & Birch

[57] ABSTRACT

A liquid detergent composition contains: (a) one or more sulfosuccinic acid monoesters represented by the general formula (I) or (II):

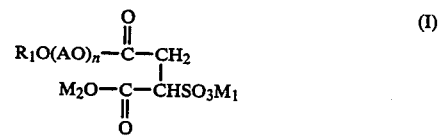

or

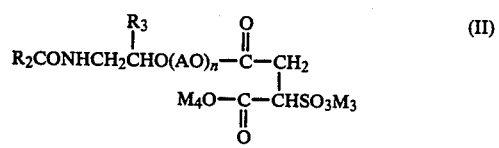

wherein each of $M_1$ to $M_4$ is H, $NH_4$, an alkali metal or a hydroxyalkyl-substituted ammonium. $R_1$ and $R_2$ are each an alkyl or hydroxyalkyl group having 8 to 20 carbon atoms on the average, $R_3$ is H or $CH_3$, AO is an oxyalkylene group having 2 or 3 carbon atoms, and n represents an integer of 0 to 20; and (b) one or more acylated compounds selected from the group consisting of acylated peptides which are obtained by hydrolyzing natural proteins so that the resultant peptides may have average molecular weights in the range of 200 to 8,000 and acylating the peptides with acylating agents having 6 to 24 carbon atoms, salts of the acylated peptides, N-acyl amino acids comprising 6 to 24 carbon atoms in the acyl group, and salts of the N-acyl amino acids.

6 Claims, No Drawings

LIQUID DETERGENT COMPOSITION

The present invention relates to liquid detergent compositions which can foam well, this being hereinafter frequently referred to as the "foaming property", and can be well rinsed, this being hereinafter frequently referred to as the "rinsing property", and are capable of imparting smoothness to the hair of skin after washing.

BACKGROUND OF THE INVENTION

When clothes, tableware or hair are washed, there have hitherto been demanded eagerly detergent compositons which can be easily rinsed so as to save time and/or quantities of water required to rinse and can give smoothness to the hair without becoming dried nor loose and to the skin without becoming dried nor rough. Few detergent compositions satisfying both of the requirements have been commercially available.

Many formulations have been attempted in order to improve the rinsing property; thus, a fatty acid soap, a nonionic material such as polyoxyethylene alkyl ether or polyoxyethylene-polyoxypropylene alkyl ether, a lower alcohol, or the like may be formulated into a detergent composition. Although the rinsing property is certainly improved in such conventional detergent compositions, the foaming property during washing will be deteriorated.

On the other hand, humidity retention agents or humectants, such as water-soluble silicone derivatives, water-soluble sugar ester derivatives, water-soluble glyceride derivatives, and the like, have been added to detergent compositions so as to impart the smoothness to the hair or skin after washing and drying. However, these agents are insufficient in their effects since they are soluble in water and hence, for the most part, removed away by rinsing. Other humidity retention agents or humectants such as propylene glycol, glycerin, ethylene glycol and the like have also been added to detergent compositions. These agents may make the hair or skin sticky although they can impart some feeling of smoothness to the hair or skin. Further, hydrocarbon oils, ester oils, silicone oils or other oils have also been known as additives to detergent compositions. Although these oils can effectively impart the smoothness to the hair or skin, they are difficult to stably formulate into liquid compositions and such formulation may deteriorate the foaming property.

SUMMARY OF THE INVENTION

Accordingly, it is an object of the present invention to provide a liquid detergent composition which has good foaming and rinsing properties and may impart a feeling of smoothness to the hair or skin without stickiness after washing and drying.

The present inventors have made a great effort to attain a detergent composition which has two important properties: that is, the composition exhibits an excellent rinsing property while its foaming property is not deteriorated; and it imparts smoothness to the hair or skin after washing and drying.

It has now been found that the aforementioned object may be attained by a novel combination of two or more specific compounds; (a) one or more sulfosuccinic acid monoesters represented by the general formula (I) or (II):

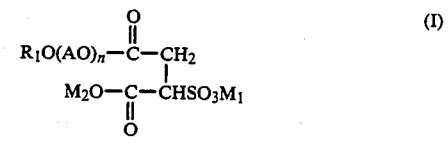

or

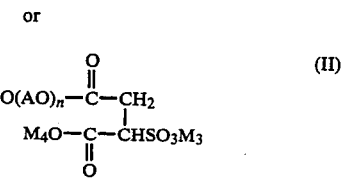

wherein each of $M_1$ to $M_4$ is H, $NH_4$, an alkali metal or a hydroxyalkyl-substituted ammonium, $R_1$ and $R_2$ are each an alkyl or hydroxyalkyl group having 8 to 20 carbon atoms on the average, $R_3$ is H or $CH_3$, AO is an oxyalkylene group having 2 or 3 carbon atoms, and n represents an integer of 0 to 20; and (b) one or more acylated compounds selected from the group consisting of acylated peptides which are obtained by hydrolyzing natural proteins so that the resultant peptides may have average molecular weights in the range of 200 to 8,000 and acylating the peptides with acylating agents having 6 to 24 carbon atoms, salts of the acylated peptides, N-acyl amino acids having 6 to 24 carbon atoms in the acyl group, and salts of the N-acyl amino acids.

According to the present invention, there is provided a liquid detergent composition utilizing both the sulfosuccinic acid monoester(s) represented by the general formula (I) or (II) above and the acylated compound(s) selected from the acylated peptides, the N-acyl amino acids, and salts thereof.

The liquid detergent compositions of this invention have good foaming and rinsing properties and can impart smoothness to the hair or skin after washing and drying by utilizing both at least one sulfosuccinic acid monoester having the specific chemical structure and at least one acylated compound selected from the acylated peptides, N-acyl amino acids and salts thereof.

The above and other objects, features and advantages of the present invention will be more apparent from the following descriptions.

DESCRIPTION OF THE INVENTION

The detergent compositions of the present invention comprise at least one sulfosuccinic acid monoester represented by the general formula (I) or (II):

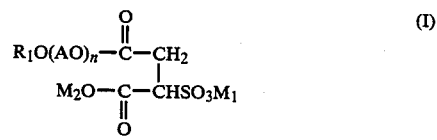

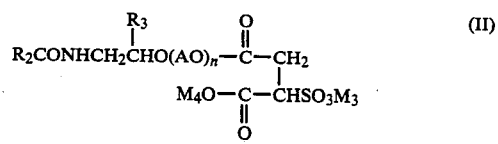

In these formulae, each of $M_1$ to $M_4$ may be selected from the group consisting of hydrogen atom, ammonium group, alkali metals and hydroxyalkyl-substituted ammonium groups. $M_1$ and $M_2$ may be the same or different from each other. Also, M₃ and M₄ may be the same or different from each other. Alkali metals may include lithium, sodium, potassium and the like. The hydroxyalkylsubstituted ammonium groups which may preferably have 1 to 3 carbon atoms in the hydroxyalkyl group may include monoethanol ammonium, diethanol ammonium, triethanol ammonium, methyl diethanol ammonium and the like. Hydrogen atom, sodium and triethanol ammonium are preferred as $M_1$ to $M_4$.

$R_1$ and $R_2$ are each straight or branched alkyl or hydroxyalkyl groups having 8 to 20 carbon atoms on the average, for example, hexyl, decyl, hydroxydecyl, dodecyl, hydroxytetradecyl, tetradecyl, nonadecyl, or the like. Any alkyl group having less than 8 or more than 20 carbon atoms may optionally be contained in the molecule, provided that the total number of carbon atoms on the average over the molecules of sulfosuccinic acid monoester contained in the detergent composition of the present invention is in the range of from 8 to 20. The number of carbon atoms on the average in such a range may give good foaming properties, whereas the number of carbon atoms on the average of either less than 8 or more than 20 will provide an insufficient foaming property of the liquid detergent composition and the object of the present invention cannot be attained.

In the formula (II), $R_3$ is either H or $CH_3$.

In the formulae, AO represents an oxyalkylene group having 2 or 3 carbon atoms, that is, oxyethylene or oxypropylene group. Both oxyethylene and oxypropylene groups may be present in the molecule.

The letter n represents an integer of 0 to 20, preferably 0 to 10. If n is more than 20, foaming properties of the resulting liquid detergent compositions may be poor.

The compounds representd by the formulae (I) and (II) may be prepared by any of known methods.

For example, the sulfosuccinic acid monoesters represented by the general formula (I) can be prepared by reacting an alkylene oxide adduct of a higher fatty acid with maleic anhydride to produce an ester of maleic anhydride and further reacting the ester of maleic anhydride with a sulfite.

On the other hand, the sulfosuccinic acid monoesters represented by the general formula (II) can be prepared by reacting a lower alcohol ester of a higher fatty acid with an alkanolamine, adding an alkylene oxide to the reaction product, further reacting the resulting addition product with maleic anhydride to produce an ester of maleic anyhydride, and reacting the ester of maleic anhydride with a sulfite.

The sulfosuccinic acid monoesters represented by the general formula (II) are more preferably used in the present invention since better results may be obtained.

The amount of the sulfosuccinic acid monoester(s) of the general formula (I) or (II) formulated into the compositions of the present invention is not especially limited but it may preferably be 1% by weight or more, more preferably 1 to 30% by weight, particularly 1 to 20% by weight based on the total weight of the composition from the practical viewpoint. If lower amounts are used, the desired results of the present invention cannot be obtained in some cases.

According to the present invention, at least one compound selected from acylated peptides, N-acyl amino acids, and salts thereof is also utilized together with the aforementioned sulfosuccinic acid monoester(s).

Acylated peptides which may be used in the present invention are those which may be obtained by hydrolyzing a naturally occurring protein to produce a peptide having an average molecular weight of 200 to 8,000, followed by acylating the peptide with an acylating agent having 6 to 24 carbon atoms. Salts of the acylated peptides include alkali metal salts, hydroxyalkyl-substituted ammonium salts and ammonium salts. The hydroxyalkyl-substituted ammonium salt may preferably have 1 to 3 carbon atoms in the hydroxyalkyl group. These acylated peptides and salts thereof may be used independently or in combination of two or more.

Illustrative examples of these compounds include N-cocoyl peptides, N-myristyl peptides, N-oleyl peptides, N-undecylyl peptides, and their alkali metal salts, hydroxyalkyl-substituted ammonium salts, and the like. In particular, N-cocoyl peptides, their alkali metal salts and hydroxyalkyl-substituted ammonium salts, and N-oleyl peptides, their alkali metal salts and hydroxyalkyl-substituted ammonium salts are preferably used in the present invention. The hydroxyalkyl substituted ammonium salts may preferably have 1 to 3 carbon atoms in the hydroxyalkyl group.

Acyl groups in the N-acyl amino acids and salts thereof which may be used in the present invention have 6 to 24 carbon atoms; for example, lauroyl, myristoyl, palmitoyl, or the like is included. The amino acids include glutamic acid, glycine, beta-alanine and the like. The salts include alkali metal salts, hydroxyalkyl-substituted ammonium salts and ammonium salts. The hydroxyalkyl substituted ammonium salts may preferably have 1 to 3 carbon atoms in the hydroxyalkyl group. N-acyl-N-alkyl amino acids are also included in the term "N-acyl amino acids" used herein. The alkyl groups in the N-acyl-N-alkyl amino acids may preferably have 1 to 3 carbon atoms and include methyl, ethyl, propyl, isopropyl and the like. These N-acyl amino acids and salts thereof may be used independently or in combination of two or more.

Preferred N-acyl amino acids and salts thereof may include N-acyl amino acids such as N-laurolylglutamic acid, N-myristoylglutamic acid, N-palmitoylaglutamic acid, N-myristoyl-beta-alamine, N-palmitoyl-beta-alanine and the like; N-acyl N-alkyl amino acids such as N-lauroyl-N-ethylglycine, N-lauroyl-N-isopropylglycine, N-lauroylsarcosine, N-myristoylsarcosine, N-palmitoylsarcosine, N-lauroyl-N-methyl-beta-alanine and the like; as well as their alkali metal salts, hydroxyalkyl-substituted ammonium salts and the likes.

Amounts of the acylated peptide(s) or salt(s) thereof and/or N-acyl amino acid(s) or salt(s) therof formulated into the composition according to the present inveniton are not particularly limited but from the practical viewpoint an amount of 0.1% by weight or more, preferably 0.1 to 20% by weight, more preferably 0.1 to 10% by weight based on the total weight of the composition may preferably be used. If lower amounts are used, the desired results of the present invention cannot be obtained in some cases.

The liquid detergent compositions of the present invention may also comprise other optional component(s) which may be commonly known and usually empolyed in conventional liquid detergents in addition to the aforementioned essential components, provided that such optional components should not affect the advantages of the present invention.

Such optional components may include anionic surfactants such as polyoxyethylene cetylether, polyoxyethylene laurylether phosphate, soap base, sodium cetylsulfate, sodium lauryl sulfate, sodium alpha-olefinic sulfonate, sodium polyoxyethylene laurylether phosphate, sodium polyoxyethylene (3) laurylether sulfate, sodium polyoxyethylene oleylether phosphate, triethanolamine lauryl sulfate, triethanolamine polyoxyethylene alkylphenylether phosphate, triethanolamine polyoxyethylene laurylether sulfate (blending amount of usually 5 to 20% by weight); nonionic surfactants such as coconut fatty acid diethanolamide, glyceryl monostearate, polyoxyethylene glyceryl monostearate, polyoxyethylene nonylphenylether including P.O.E (6.5) nonylphenylether, polyoxyethylene octylphenylether, polyoxyethylene sorbitan monolaurate (20 E.O.), polyoxyethylene sorbitan monooleate (6 E.O.), polyoxyethylene sorbitan monooleate (20 E.O.), polyoxyethylene sorbitan monostearate (6 E.O.), sorbitan monolaurate, sorbitan monooleate, sorbitan monopalmitate, sorbitan monostearate (blending amount of usually 1 to 10% by weight); cationic surfactants such as dodecyldimethyl-2-phenoxyethylammonium chloride, stearyldimethylbenzylammonium chloride, stearyltrimethylammonium chloride, distearyltrimethylammonium chloride (blending amount of usually 1 to 10% by weight); amphoteric surfactants such as coco-betaine, N-lauryl-2-hydroxypropyl-sulfobetaine, sodium methyl cocoyl taurate, sodium-2-cocoalkyl-1-carboxyethyl-1-hydroxyethylimidazolinium, sodium beta-laurylaminopropionate (blending amount of usually 1 to 10% by weight); thickeners such as methyl cellulose, hydroxypropyl cellulose, hydroxyethyl cellulose, cationized cellulose, polyethylene glycol, fatty acid esters of polyethylene glycol, and the like; humidity retention agents or humectants such as ethylene glycol, propylene glycol, 1,3-butylene glycol, glycerin, sorbitol, and the like; vitamins such as vitamin E, vitamin C, vitamin E acetic acid ester, and the like; cold- or hot-sensitive agents such as peppermint, capsicum tincture, and the like; inorganic builders such as sodium tripolyphosphate, sodium metasilicate, mirabilite, and the like; germicides; solubilizers; softening agents; ultraviolet radiation absorbers; chelating agents; viscosity controlling agents; colorants; perfumes; and the likes. These agents may be used independently or, if desired, in combination of two or more.

The present invention will be illustrated by the following examples together with comparative examples. These examples should not be construed as limiting the present invention.

The criteria used in the examples to estimate and/or evaluate the properties of the detergent compositions are as follows:

Foaming

Twenty milliliters (20 ml) of a sample of liquid detergent composition in the form of 6% aqueous solution was taken in a 100 ml cylinder at 25° C. After adding 0.2 g of liquid lanolin as an artificial stain, the cylinder was agitated 20 times per 10 seconds and the volume of foam (in ml) after one minute was measured and evaluated according to the following criteria:

| Criteria: | Volume of foam |
|---|---|
| ⊚ | 50 ml or more |
| ○ | 40 to 49 ml |
| △ | 30 to 39 ml |
| x | 20 to 29 ml |
| xx | 19 ml or less |

Smoothness of the hair

A liquid detergent composition (0.6 g) was applied to a bundle of hair (10 g) and the bundle of hair was washed by rubbing. The bundle of hair was rinsed by agitating 30 times per 30 seconds in a beaker containing 500 g of city water and squeezed lightly. These rinsing procedure was repeated an additional four times. The bundle of hair was then dried a whole day and night in a room adjusted to 25° C. and 65% RH. A organoleptic test by 20 panelists was carried out to evaluate the smoothness of the hair by using a standard sample comprising 20% of polyoxyethylene (3) lauryl ether sodium sulfate and the balance of water. The results were evaluated according to the criteria given below.

Rinsing

In the experiments for evaluating the smoothness of the hair, another organoleptic test by 20 panelists was also performed to evaluate the state of foam in, the degree of cloudiness of, and the transparency of the city water during the rinsing procedure by using the same standard sample. The results were evaluated according to the following criteria:

| Criteria for evaluating the smoothness of hair and rinsing: | |
|---|---|
| 5 | A test sample was more excellent with the significance level of 1% |
| 4 | A test sample was more excellent with the significance level of 5% |
| 3 | There was no significant difference between a test sample and the standard sample |
| 2 | The standard sample was more excellent with the significance level of 5% |
| 1 | The standard sample was more excellent with the significance level of 1% |

Examples 1–12 and COMPARATIVE EXAMPLES 1–4

Samples of liquid detergent composition were prepared and the foaming and rinsing properties and the smoothness of the hair were tested as described above. Compositions of these samples are shown in Table 1.

The results are also shown in Table 1.

TABLE 1

| | Standard sample | Example | | | | | | | | | | | | Comparative example | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 1 | 2 | 3 | 4 |
| Sodium polyoxyethylene (3) lauryl ether sulfate | 20 | 15 | 15 | 15 | 15 | 15 | 15 | 15 | | | | | 5 | 15 | 15 | | |
| Sodium C$_{14}$-alpha-olefin sulfonate | | | | | | | | | | 15 | | | | | | | |
| Sodium linear alkyl benzene sulfonate | | | | | | | | | | | 15 | | | | | | |
| Disodium sulfosuccinate coconut oil alkyl monoester | 3 | | | | | | | | | | | | | | | | |
| Disodium sulfosuccinate polyoxyethylene (6) coconut oil alkyl monoester | | | | 3 | | | | | | | | | | | | | |
| Disodium sulfosuccinate polyoxyethylene | | | | | 3 | | | | | | | | | | | | |

TABLE 1-continued

| | Standard sample | \multicolumn{12}{c}{Example} | | | | | | | | | | | | | Comparative example | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 1 | 2 | 3 | 4 |
| (1) coconut oil fatty acid amide monoester Disodium sulfosuccinate polyoxyethylene | | | | | 3 | 3 | 3 | 3 | 3 | 3 | 10 | 15 | 10 | | 3 | | 15 |
| (6) coconut oil fatty acid amide monoester Sodium N—cocoyl peptide (molecular weight: 650) | | 2 | 2 | 2 | 2 | | | | 2 | 2 | 10 | 5 | 5 | 2 | | 15 | |
| Sodium N—oleyl peptide (molecular weight: 1700) | | | | | | 2 | | | | | | | | | | | |
| Triethanolamine N—lauroylglutamate | | | | | | | 2 | | | | | | | | | | |
| Sodium N—lauroylsarcosine | | | | | | | | 2 | | | | | | | | | |
| Purified water | Balance | → | → | → | → | → | → | → | → | → | → | → | → | → | → | → | → |
| Total | 100.0% | → | → | → | → | → | → | → | → | → | → | → | → | → | → | → | → |
| Foaming | O | ◎ | ◎ | ◎ | ◎ | ◎ | ◎ | ◎ | ◎ | ◎ | ◎ | ◎ | ◎ | ◎ | ◎ | ◎ | ◎ |
| Rinsing | 3 | 4 | 4 | 5 | 5 | 5 | 5 | 5 | 5 | 5 | 5 | 5 | 5 | 3 | 3 | 3 | 3 |
| Smoothness of the hair | 3 | 4 | 4 | 5 | 5 | 5 | 5 | 5 | 5 | 5 | 5 | 5 | 5 | 3 | 3 | 3 | 3 |

As will be seen from the results shown in Table 1, the liquid detergent compositions of Examples 1–12 according to the present invention showed the substantially same foaming level and the more excellent rinsing property and smoothness of the hair after washing and drying as compared with the standard sample. However, the liquid detergent compositions of Comparative Examples 1 and 3 which contained no sulfosuccinic acid monoester or those of Comparative Examples 2 and 4 which contained no acylated peptide nor N-acyl amino acid gave no significant improvement in the rinsing property and the smoothness of the hair after washing and drying as compared with the standard sample.

EXAMPLES 13-16

Liquid detergent compositions shown in Table 2 were prepared and the foaming and rinsing properties and the smoothness of the hair after washing and drying were evaluated as in the foregoing Examples and Comparative Examples.

The results are listed in Table 2.

TABLE 2

| | \multicolumn{4}{c}{Example} | | | |
|---|---|---|---|---|
| | 13 | 14 | 15 | 16 |
| Sodium polyoxyethylene (3) lauryl ether sulfate | 10 | | 5 | 10 |
| Sodium $C_{14}$-alpha-olefin sulfonate | | 10 | 5 | |
| Disodium sulfosuccinate polyoxyethylene (6) layroyl amide monoester | 3 | 5 | 5 | 5 |
| Sodium N—cocoyl peptide (molecular weight 650) | 2 | 1 | 1 | 1 |
| Coconut oil fatty acid diethanolamide | 5 | 5 | 5 | 5 |
| Anhydrous sodium sulfate | 2 | 2 | 2 | 2 |
| Sodium lauryl sulfate | 2 | 2 | 2 | 2 |
| Quaternary nitrogen-containing cellulose ether (nitrogen content of 1.5% and molecular weight of 200,000) | 1 | 1 | 1 | 1 |
| Polyoxyethylene-modified silicone | 1 | 1 | 1 | 1 |
| Citric acid monohydrate | 0.1 | 0.1 | 0.1 | 0.1 |
| Oxybenzone | 0.1 | 0.1 | 0.1 | 0.1 |
| Perfume | 0.5 | 0.5 | 0.5 | 0.5 |
| Pigment | 0.001 | 0.001 | 0.01 | 0.01 |
| Purified water | Balance | Balance | Balance | Balance |
| Total | 100.0% | 100.0% | 100.0% | 100.0% |
| Foaming | ◎ | ◎ | ◎ | ◎ |
| Rinsing | 5 | 5 | 5 | 5 |
| Smoothness of the hair | 5 | 5 | 5 | 5 |

As will be seen from the results shown in Table 2, the liquid detergent compositions which also contained a perfume, pigment, polymer or the like showed the substantially same foaming property and the more excellent rinsing property and smoothness of the hair as compared with the standard sample. Thus, such an additive did not affect the advantages of the liquid detergent compositions according to the present invention.

What is claimed is:

1. A liquid detergent composition which comprises
(a) 1 to 30% by weight of one or more sulfosuccinic acid monoesters represented by the general formula (I) or (II):

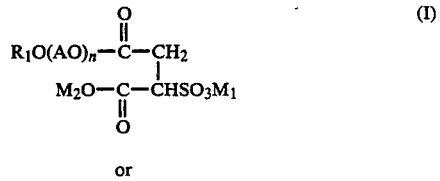

(I)

or

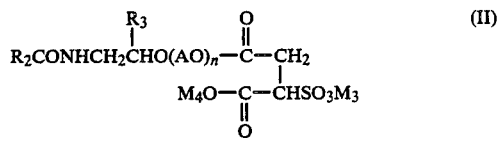

(II)

wherein each of $M_1$ to $M_4$ is H, $NH_4$, an alkali metal or a hydroxyalkyl-substituted ammonium, $R_1$ and $R_2$ are each an alkyl or hydroxyalkyl group having 8 to 20 carbon atoms on the average, $R_3$ is H or $CH_3$, AO is an oxyalkylene group having 2 or 3 carbon atoms, and n represents an integer of 0 to 20; and (b) 0.1 to 20% by weight of one or more acylated compounds selected from the group consisting of acylated peptides which are obtained by hydrolyzing natural proteins so that the resultant peptides have average molecular weights in the range of 200 to 8,000 and acylating the peptides with acylating agents having 6 to 24 carbon atoms, alkali metal salts and hydroxyalkyl-substituted ammonium salts of the acylated peptides, N-acyl amino acids comprising 6 to 24 carbon atoms in the acyl group, and alkali metal salts and hydroxyalkyl substituted ammonium salts of the N-acyl amino acids, all percentages based on the total weight of the composition.

2. The liquid detergent composition according to claim 1, wherein the acylated compound is selected from the group consisting of N-cocoyl peptides, N-myristyl peptides, N-oleyl peptides, N-undecylyl peptides, N-lauroylglutamic acid, N-myristoylglutamic acid, N-palmitoylglutamic acid, N-myristoyl-beta-alanine, N-palmitoyl-beta-alanine, N-lauroyl-N-ethyl-glycine, N-lauroyl-N-isopropylglycine, N-lauroylsarcosine, N-myristoylsarcosine, N-palmitoylsarcosine and N-lauroyl-N-methyl-beta-alanine and their alkali metal salts and hydroxylalkyl-substituted ammonium salts, and mixtures thereof.

3. The liquid detergent composition according to claim 1, wherein n is an integer of 0 to 10.

4. The liquid detergent composition according to claim 1, wherein said sulfosuccinic acid monoester has the formula (II).

5. The liqid detergent composition according to claim 1, wherein said sulfosuccinic acid monoester is present in an amount of 1 to 20% by weight.

6. The liquid detergent composition according to claim 1, wherein the amount of said acylated compound is 0.1 to 10% by weight.

* * * * *